United States Patent [19]

Romano et al.

[11] 4,326,079

[45] Apr. 20, 1982

[54] PROCESS FOR PREPARING AROMATIC ALKYLAMINES

[75] Inventors: Ugo Romano, Vimercate; Giuseppe Iori, San Donato Milanese, both of Italy

[73] Assignee: Anic, S.P.A., Palermo, Italy

[21] Appl. No.: 123,918

[22] Filed: Feb. 22, 1980

[30] Foreign Application Priority Data

Mar. 7, 1979 [IT] Italy .............................. 20800 A/79

[51] Int. Cl.$^3$ ...................... C07C 85/02; C07C 85/08
[52] U.S. Cl. .................................................. 564/393
[58] Field of Search ........................ 260/577, 583 L; 564/393, 468

[56] References Cited

U.S. PATENT DOCUMENTS

| | | | |
|---|---|---|---|
| 2,187,745 | 1/1940 | Lazier | 260/583 L X |
| 2,944,082 | 7/1960 | Class | 260/583 L |

FOREIGN PATENT DOCUMENTS

| | | | |
|---|---|---|---|
| 2160111 | 8/1972 | Fed. Rep. of Germany | 260/577 |
| 2618033 | 10/1977 | Fed. Rep. of Germany | 260/577 |
| 165462 | 10/1964 | U.S.S.R. | 260/577 |
| 539031 | 12/1976 | U.S.S.R. | 260/577 |

OTHER PUBLICATIONS

Vizgert et al., "J. Org. Chem., USSR", vol. 5, pp. 914–919 (1969).
Ptitsyna et al., "J. Org. Chem., USSR", vol. 6, pp. 1367–1370 (1970).

*Primary Examiner*—John Doll
*Attorney, Agent, or Firm*—Morgan, Finnegan, Pine, Foley and Lee

[57] ABSTRACT

Aromatic alkylamines are prepared by reacting an amine with an alkyl ester of carbonic acid in the presence of an organic iodide, at a temperature below 150° C.

6 Claims, No Drawings

PROCESS FOR PREPARING AROMATIC ALKYLAMINES

This invention relates to a process for preparing N-alkylarylamines by the alkylation of aromatic amines with a dialkylester of carbonic acid in the presence of a catalytic quantity of an organic iodide.

The N-alkylation of aromatic amines is usually carried out by sulphuric acid esters or hydrogen halogen acid esters.

This leads to problems of corrosion, high toxicity and pollution due to the neutralisation of the acids released by the reaction.

It is also known (Ger. Off. No. 2,160,111 published Apr. 1, 1976) that the reaction between aromatic amines and dialkyl carbonates at a temperature below 150° C. leads to the formation only of minimum quantities of urethanes if Lewis acids are absent, or to the formation of urethanes (yields less than 50%), N-alkylamines (yield less than 10%) and urea traces if Lewis acids are present.

It is also known (Ger. Off. No. 2,168,033 published Nov. 10, 1977) that if a primary or secondary aromatic amine is reacted with a large excess of dialkyl carbonate in the absence of Lewis acids at a tempeature above 150° C. for a time of 3 to 10 hours, only N-alkylamines are obtained at a yield of between 30 and 98%.

We have now discovered that if an aromatic amine is reacted with a dialkyl carbonate in the presence of a catalytic quantity of an organic iodide at a temperature less than 150° C., the relative N-alkylamine is obtained at nearly a total yield after a time of between 3 and 5 hours according to the amine to be alkylated. This forms the subject matter of the present invention.

The methylation is carried out in a stainless steel autoclave with stirring at a temperature (less than 150° C.) and for a time (3–5 hours) depending upon the amine to be alkylated. The reagent ratio is chosen according to the number of hydrogens to be substituted in the amine, favoring mono or polysubstitution, according to the actual case concerned.

Some examples are given hereinafter which are non-limitative examples of the present invention.

EXAMPLE 1

10 grams of aniline, 22 grams of dimethyl carbonate and 0.16 gram of methyl iodide were fed into an autoclave at 148° C. for 5 hours.

The aniline conversion was total.

The excess dimethyl carbonate and the methanol formed were distilled off at atmospheric pressure.

The residue consisted of 11.1 grams of N,N-dimethylaniline (selectivity 85%) and 1.7 grams of N-methylaniline (selectivity 15%).

EXAMPLE 2

The test of example 1 was carried out at 138° C. for 7 hours. Aniline conversion was 80%, with selectivity of 70% towards N,N-dimethylaniline and 30% towards N-methylaniline.

EXAMPLE 3

10 grams of p-toluidine, 20 grams of dimethyl carbonate and 0.15 gram of $CH_3I$ were fed into an autoclave at 148° C. for 5 hours. The p-toluidine conversion was total. The selectivity was 85% towards N,N-dimethyl-p-toluidine and 15% towards N-methyl-p-toluidine.

EXAMPLE 4

13.6 grams of m-Cl-aniline, 22 grams of dimethyl carbonate and 0.15 gram of $CH_3I$ were fed into an autoclave at 147° C. for 5 hours. Conversion was 90%, with selectivity of 80% towards N,N-dimethyl-m-chloroaniline and 20% towards N-methyl-m-Cl-aniline.

We claim:

1. A process for preparing aromatic alkylamines consisting of reacting the relevant amine with a dialkylester of carbonic acid in the presence of an organic iodide and forming the relevant aromatic alkylamine.

2. A process for preparing aromatic alkylamines according to claim 1, wherein the reaction is carried out at a temperature less than 150° C.

3. A process for preparing aromatic alkylamines consisting of reacting the relevant amine with a dialkylester of carbonic acid in the presence of an organic iodide at a temperature less than 150° C. for a time between 3 and 5 hours and forming the relevant aromatic amine.

4. A process according to claim 3 wherein the amine is aniline and carbonic acid ester is dimethyl carbonate.

5. A process according to claim 3 wherein the amine is p-toluidine and the carbonic acid ester is dimethyl carbonate.

6. A process according to claim 3 wherein the amine is m-chloro-aniline and the carbonic acid ester is dimethyl carbonate.

* * * * *